United States Patent [19]

Errico et al.

[11] Patent Number: 5,584,834
[45] Date of Patent: Dec. 17, 1996

[54] POLYAXIAL LOCKING SCREW AND COUPLING ELEMENT ASSEMBLY FOR USE WITH SIDE LOADING ROD FIXATION APPARATUS

[75] Inventors: Joseph P. Errico, Hempstead, N.Y.; Thomas J. Errico, Summit; James D. Ralph, Oakland, both of N.J.

[73] Assignee: Fastenetix, L.L.C., Summit, N.J.

[21] Appl. No.: 502,809

[22] Filed: Jul. 14, 1995

Related U.S. Application Data

[63] Continuation-in-part of Ser. No. 502,285, Jul. 13, 1995.

[51] Int. Cl.$^6$ ............................................... A61B 17/70
[52] U.S. Cl. ..................................... 606/61; 606/73
[58] Field of Search ............................ 606/61, 69, 70, 606/71, 72, 73, 66, 65, 60, 59, 54, 104

[56] References Cited

U.S. PATENT DOCUMENTS

| | | | |
|---|---|---|---|
| 4,805,602 | 2/1989 | Puno et al. . | |
| 4,946,458 | 8/1990 | Harms et al. | 606/61 |
| 4,987,892 | 1/1991 | Krag et al. | 606/61 |
| 5,151,103 | 9/1992 | Tepic et al. | 606/69 |
| 5,176,680 | 1/1993 | Vignaud et al. | 606/61 |
| 5,190,543 | 3/1993 | Schläpfer | 606/61 |
| 5,207,678 | 5/1993 | Harms et al. | 606/61 |
| 5,217,497 | 6/1993 | Mehdian | 623/17 |
| 5,261,909 | 11/1993 | Sutterlin et al. | 606/61 |
| 5,261,912 | 11/1993 | Frigg | 606/61 |
| 5,306,275 | 4/1994 | Bryan | 606/61 |
| 5,360,431 | 11/1994 | Puno et al. | 606/72 |
| 5,443,467 | 8/1995 | Biedermann et al. | 606/65 |
| 5,480,401 | 2/1996 | Navas | 606/61 |

*Primary Examiner*—Guy V. Tucker
*Attorney, Agent, or Firm*—Joseph P. Errico

[57] ABSTRACT

A polyaxial orthopedic device for use with rod implant apparatus includes a screw having a curvate head and a coupling element. The coupling element has a tapered lower portion including a slotted interior chamber in which the curvate head is initially polyaxially disposed. The coupling element further includes a recess formed in its side for receiving a rod of an implant apparatus, and an exterior threading disposed on its upper portion onto which a locking nut may be downwardly translated. A hollow cylindrical rod securing sleeve fits above the rod receiving recess, having a pair of grooves formed in its lower surface for seating against the rod. A locking collar is disposed below the rod receiving recess, having a pair of grooves in its top surface for receiving thereon the rod. Both the sleeve and the collar are axially translatable along the exterior surface of the coupling element. The downward translation of the collar provides an inward force on the outwardly tapered portion upon downward translation thereof, thereby causing the vertical slots to close, and crush locking the screw head within the interior chamber. The downward translation of the locking nut locks the rod between the sleeve and the collar, and the screw in the interior chamber.

13 Claims, 5 Drawing Sheets

POLYAXIAL LOCKING SCREW AND COUPLING ELEMENT ASSEMBLY FOR USE WITH SIDE LOADING ROD FIXATION APPARATUS

CROSS-REFERENCE TO PRIOR APPLICATION

This application is a continuation-in-part of prior application U.S. Ser. No. 08/502,285, entitled "An Advanced Polyaxial Locking Screw And Coupling Element For Use With Rod Fixation Apparatus", filed Jul. 13, 1995, still pending.

BACKGROUND OF THE INVENTION

1. Field of the Invention

This invention relates generally to a polyaxial screw and coupling apparatus for use with orthopedic fixation systems. More particularly, the present invention relates to a screw for insertion into spinal bone, and a coupling element polyaxially mounted thereto for coupling the screw to an orthopedic implantation structure, such as a rod, therein enhancing the efficacy of the implant assembly by providing freedom of angulation among the rod, screw and coupling element.

2. Description of the Prior Art

The spinal column is highly complex system of bones and connective tissues which houses and protects critical elements of the nervous system and the arterial and veinous bodies in close proximity thereto. In spite of these complexities, the spine is a highly flexible structure, capable of a high degree of curvature and twist through a wide range of motion.

Genetic or developmental irregularities, trauma, chronic stress, tumors, and disease, however, can result in spinal pathologies which either limit this range of motion, or which threaten the critical elements of the nervous system housed within the spinal column. A variety of systems have been disclosed in the art which achieve this immobilization by implanting artificial assemblies in or on the spinal column. These assemblies may be classified as anterior, posterior, or lateral implants. As the classification suggests, lateral and anterior assemblies are coupled to the anterior portion of the spine, which is the sequence of vertebral bodies. Posterior implants are attached to the back of the spinal column, generally hooking under the lamina and entering into the central canal, attaching to the transverse process, or coupling through the pedicle bone. The present invention relates to spinal fixation devices for immobilizing and altering the alignment of the spine over a large number, for example more than three or four, vertebra by means of affixing at least one elongate rod to the sequence of selected bones.

Such "rod assemblies" generally comprise a plurality of screws which are implanted through the posterior lateral surfaces of the laminae, through the pedicles, and into their respective vertebral bodies. The screws are provided with coupling elements, for receiving an elongate rod therethrough. The rod extends along the axis of the spine, coupling to the plurality of screws via their coupling elements. The aligning influence of the rod forces the spine to which it is affixed, to conform to a more proper shape.

It has been identified, however, that a considerable difficulty is associated with inserting screws along a misaligned curvature and simultaneously exactly positioning the coupling elements such that the receiving loci thereof are aligned so that the rod can be passed therethrough without distorting the screws. Attempts at achieving proper alignment with fixed screws is understood to require considerably longer operating time, which is known to increase the incidence of complications associated with surgery. Often such alignmeats, with such fixed axes devices could not be achieved, and the entire instrumentationing effort would end unsuccessfully.

In addition, for many patients specific pathology it is desirable that the rod extend down into and beyond the lumbar portion of the spine, and for the end of the rod to be coupled to the sacral bone. Providing such an end to the assembly in the sacral bone has been understandably suggested inasmuch as it provides superior support to the full extent of the assembly. The most suitable position for the insertion of the screws into the sacral body may not, however, conform to the direction extent of the rod as it is affixed to the entirety of the assembly. Misalignment of the rod with respect to the screw and the coupling element is often a source of considerable disadvantage for the surgeon, often requiring considerable efforts to be expended bending and aligning the rod with the receiving locus of the coupling element. These additional efforts are a considerable difficulty associated with the proper and expeditious affixation, and over the long term, the offset of the rod can have a deleterious effect on the overall performance of the entire implantation assembly.

The art contains a variety of attempts at providing instrumentation which permit a freedom with respect to angulation of the screw and the coupling element. These teachings, however, have generally been complex, and inadequately reliable with respect to durability. The considerable drawbacks associated with the prior art systems include complexity, difficulty properly positioned the rod and coupling elements, and the tedious manipulation of the many parts associated with the complex devices.

It is, therefore, the principal object of the present invention to provide a pedicle screw and coupling element assembly which provides a polyaxial freedom of implantation angulation with respect to rod reception.

In addition, it is an object of the present invention to provide such an assembly which comprises a reduced number of elements, and which correspondingly provides for expeditious implantation.

Accordingly it is also an object of the present invention to provide an assembly which is reliable, durable, and provides long term fixation support.

Other objects of the present invention not explicitly stated will be set forth and will be more clearly understood in conjunction with the descriptions of the preferred embodiments disclosed hereafter.

SUMMARY OF THE INVENTION

The preceding objects of the invention are achieved by the present invention which is a polyaxial locking screw and coupling element for use with rod stabilization and immobilization systems in the spine. More particularly, the polyaxial screw and coupling element assembly of the present invention comprise a bone screw having a head which is curvate in shape, for example semi-spherical, and a coupling element mounted thereon so as to be free to rotate prior to the secure fixation of the rod thereto, and which may be securely locked in a given angulation once the rod is received by the coupling element. The coupling element has a generally cylindrical main body portion, a locking collar, a removable external rod securing sleeve, and a top locking nut.

The coupling element may be conceptually divided into a lower socket portion, an intermediate rod receiving portion, and a top nut receiving portion. The lower socket portion includes an interior chamber having an opening at the bottom thereof. The interior chamber is ideally suited for receiving therein the head of the screw such that the screw and the coupling element are held together in a rotationally and angularly free relationship. The external surface of the socket portion includes at least one vertical slot which is provided so that the opening in the bottom of the element may expand to receive the head of the screw, which has a major diameter which is larger than the unexpanded opening, such that the head of the screw may enter into the interior chamber. The at least one slot resiliently expands to permit the head of the screw to enter, and subsequently contracts into its original position once the head is fully inserted, therein inhibiting the screw head from being retracted. The head of the screw and the interior chamber are, however, free to rotate and angulate relative to one another.

The exterior of the lower portion of the coupling element, into which the screw head is inserted, tapers outward slightly toward the bottom of the element, therein having a slightly wider diameter at the bottom than at the top thereof. A locking collar, having a diameter equal to, or slightly larger than the top of the lower portion, but less than the diameter of the bottom of the lower portion, is initially disposed about the coupling element with the bottom of the locking collar resting against the widening surface of the element. The top of the collar includes two opposing grooves, or notches, onto which the rod is initially placed. Displacement of the locking collar downward causes the at least one vertical slot in the lower portion of the coupling element to close, therein causing the inner surface of the interior chamber to move radially inward, contacting the head of the screw, and locking thereto, thereby inhibiting further swingability, The intermediate portion of the coupling element comprises a side receiving channel wherein the rod of the implant apparatus is mounted. More particularly, at a position above the lower portion, a channel is formed in the side of the generally cylindrical body, therein providing a receiving locus into which a support rod may nest. In order that the rod may be securely held within the receiving locus, an external rod securing sleeve is provided. The external rod securing sleeve is generally cylindrical in shape, having a hollow center for sliding over the top of the coupling element. The bottom of the cylindrical sleeve includes opposing grooves, similar to the grooves in the top of the locking collar. The grooves are positioned and designed to mate with the top of the rod, and to lock thereto upon the application of a downward force. The grooves of the sleeve, however, are preferably deeper than those of the locking collar, enabling the sleeve to encompass a larger angular section of the rod, thereby securely locking the rod in the rod receiving locus between the grooves of the sleeve and the grooves of the locking collar. In addition, the receiving locus is necessarily wider than the rod which is to be placed therein. This dimension relationship is required so that the sleeve may be forced down onto the rod, and that the rod may in turn force the locking collar downward. The rod, therefore, must be able to translate downward relative to the coupling element, within the receiving locus.

The upper portion of the coupling element comprises a threading onto which a locking nut may be inserted, therein providing a downward force onto the rod securing sleeve. The downward force of the sleeve is translated to a downward force of the rod, and on the locking collar. The locking collar is forced downward by the rod, and locks the screw in the interior chamber of the coupling element.

Each portion of the coupling element (lower, intermediate, and upper) includes a central bore, aligned with one another, and which extends axially from the top of the coupling element into the interior chamber. The screw head correspondingly includes a recess, which is alignable with the central bore of the coupling element, whereby a screw-driving instrument may be inserted through the central bore, into the recess in the screw, and utilized to drive the screw into the bone.

The first step in the process of implanting this embodiment of the invention is to insert the head of the screw into the interior chamber of the coupling element. Once it has been inserted, the angle of insertion at which the screw will have the greatest holding strength relative to the loading which the rod system will be applying thereto must be determined. Once this angle has been found, the screw and the coupling element are aligned with respect to one another so that a screw-driving tool may be inserted down the central bore of the coupling element, into the recess in the head of the screw, and thereby be rotationally inserted into the bone. Subsequent to the insertion of the screw, the screw-driving device is removed from the assembly, therein permitting the coupling element to rotate and change angular alignment relative to the screw.

In this position, the locking collar of the coupling element has not yet been forced downward to lock the screw to the coupling element. The top of the locking collar extends upward, beyond the top of the lower section, and is disposed above the lower lip of the receiving channel. The rod of the implantation apparatus is then provided into the side receiving locus, and is positioned so that it rests snugly within the opposing grooves of the top of the locking collar. Once the rod has been properly positioned, the securing sleeve is placed onto the coupling element, with the top of the rod resting in the opposing grooves thereof. The top locking nut is then introduced onto the top of the coupling element.

The final act of driving the top locking nut down onto the upper portion of the coupling element causes the rod securing sleeve to fully descend, therein translating the rod and the locking collar therebelow downward, locking the rod between the two pair of grooves of the sleeve and the locking collar, respectively, and causing the locking collar to secure the angulation of the coupling element to the head of the screw.

In addition, it shall be understood that the curvate shape of the head of the screw may be chosen from the various specific shapes which are compatible with the general polyaxial concept of the present invention. For the purposes of providing specific variations of the embodiments described above, and set forth more fully hereinbelow with respect to the drawings, the shape of the screw head is semi-spherical. However, it is understood that one skilled in the art could easily alter the shape of the head, for example to have a flat top. The choice of using flattened top profile versus a fully semi-spherical profile may be associated with the height of the overall screw and coupling element, the semi-spherical (or ball) head of the screw providing for a higher seating of the coupling element versus the hemi-spherical flattened head.

Multiple screw and coupling element assemblies are generally necessary to complete the full array of anchoring sites for the rod immobilization system, however, the screw and coupling element assembly of the present invention is designed to be compatible with alternative rod systems so that, where necessary, the present invention may be employed to rectify the failures of other systems the implantation of which may have already begun.

DETAILED DESCRIPTION OF THE PREFERRED EMBODIMENT

While the present invention will be described more fully hereinafter with reference to the accompanying drawings, in which particular embodiments and methods of implantation are shown, it is to be understood at the outset that persons skilled in the art may modify the invention herein described while achieving the functions and results of this invention. Accordingly, the descriptions which follow are to be understood as illustrative and exemplary of specific structures, aspects and features within the broad scope of the present invention and not as limiting of such broad scope.

Figure 1:
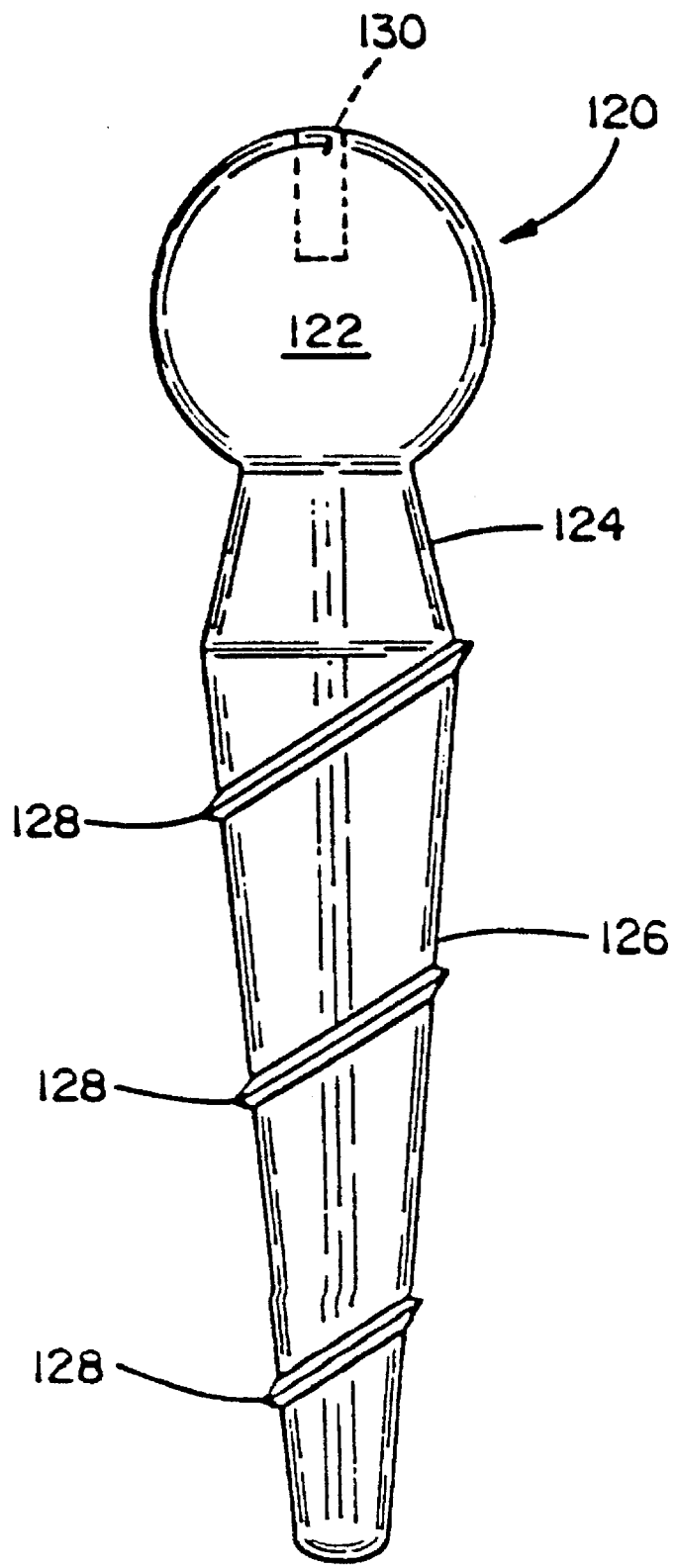
FIG. 1 is a side view of a screw having a curvate head which is an aspect of the present invention.

Referring now to FIG. 1, a side view of the screw portion of the present invention, comprising a curvate head, is shown. The screw 120 comprises a head portion 122, a neck 124, and a shaft 126. In FIG. 1, the shaft 126 is shown as having a tapered shape with a high pitch thread 128. It shall be understood that a variety of shaft designs are interchangeable with the present design. The specific choice of shaft features, such as thread pitch, shaft diameter to thread diameter ratio, and overall shaft shape, should be made be the physician with respect to the conditions of the individual patient's bone, however, this invention is compatible with a wide variety of shaft designs.

The head portion 122 of the screw 120 comprises a semi-spherical shape, which has a recess i30 in it. It is understood that the semi-spherical shape is a section of a sphere, in the embodiment shown the section is greater in extent than a hemisphere, and it correspondingly exhibits an external contour which is equidistant from a center point of the head. In a preferred embodiment, the major cross-section of the semi-spherical head 122 (as shown in the two dimensional illustration of FIG. 5) includes at least 270 degrees of a circle.

The recess 130 defines a receiving locus for the application of a torque for driving the screw 120 into the bone. The specific shape of the recess 122 may be chosen to cooperate with any suitable screw-driving tool. For example, the recess 130 may comprise a slot for a flat-headed screwdriver, a crossed recess for a phillips head screwdriver, or most preferably, a hexagonally shaped hole for receiving an allen wrench. It is further preferable that the recess 130 be co-axial with the general elongate axis of the screw 120, and most particularly with respect to the shaft 126. Having the axes of the recess 130 and the shaft 126 co-linear facilitates step of inserting the screw 120 into the bone.

Figure 7:
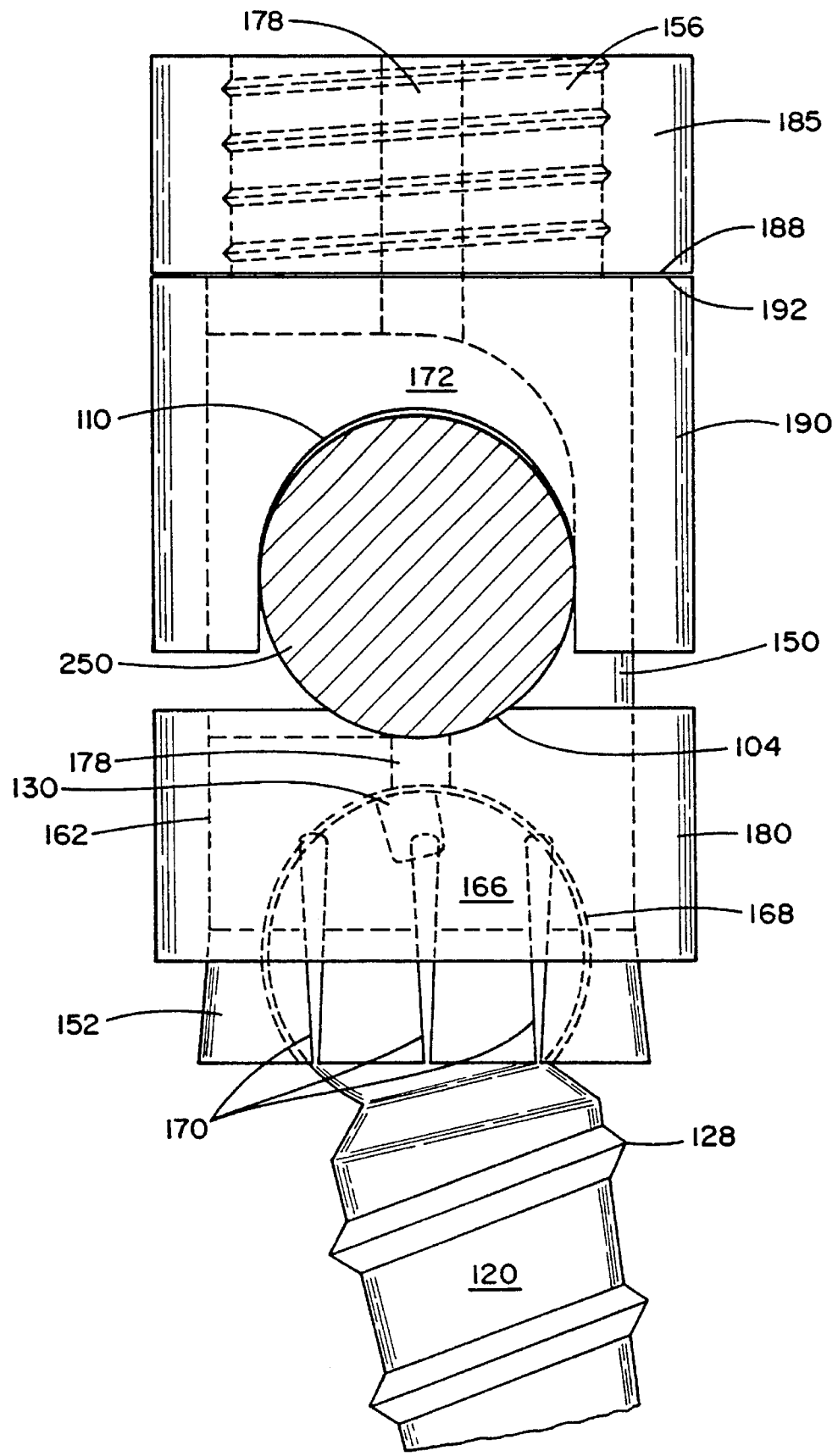
FIG. 7 is a side cross-sectional view of the first embodiment of the present invention in its fully assembled disposition having a rod securely locked therein.

The semi-spherical head portion 122 is connected to the shaft 126 at a neck portion 124. While it is preferable that the diameter of the shaft 126 be less than the diameter of the semi-spherical head 122, it is also preferable that the neck 124 of the screw 120 be narrower than the widest portion of the shaft 126. This preferable dimension permits the screw to be locked at a variety of angles while still being securely joined to the coupling element (embodiments of which are shown in FIGS. 2, 3 and 7).

Figure 2:
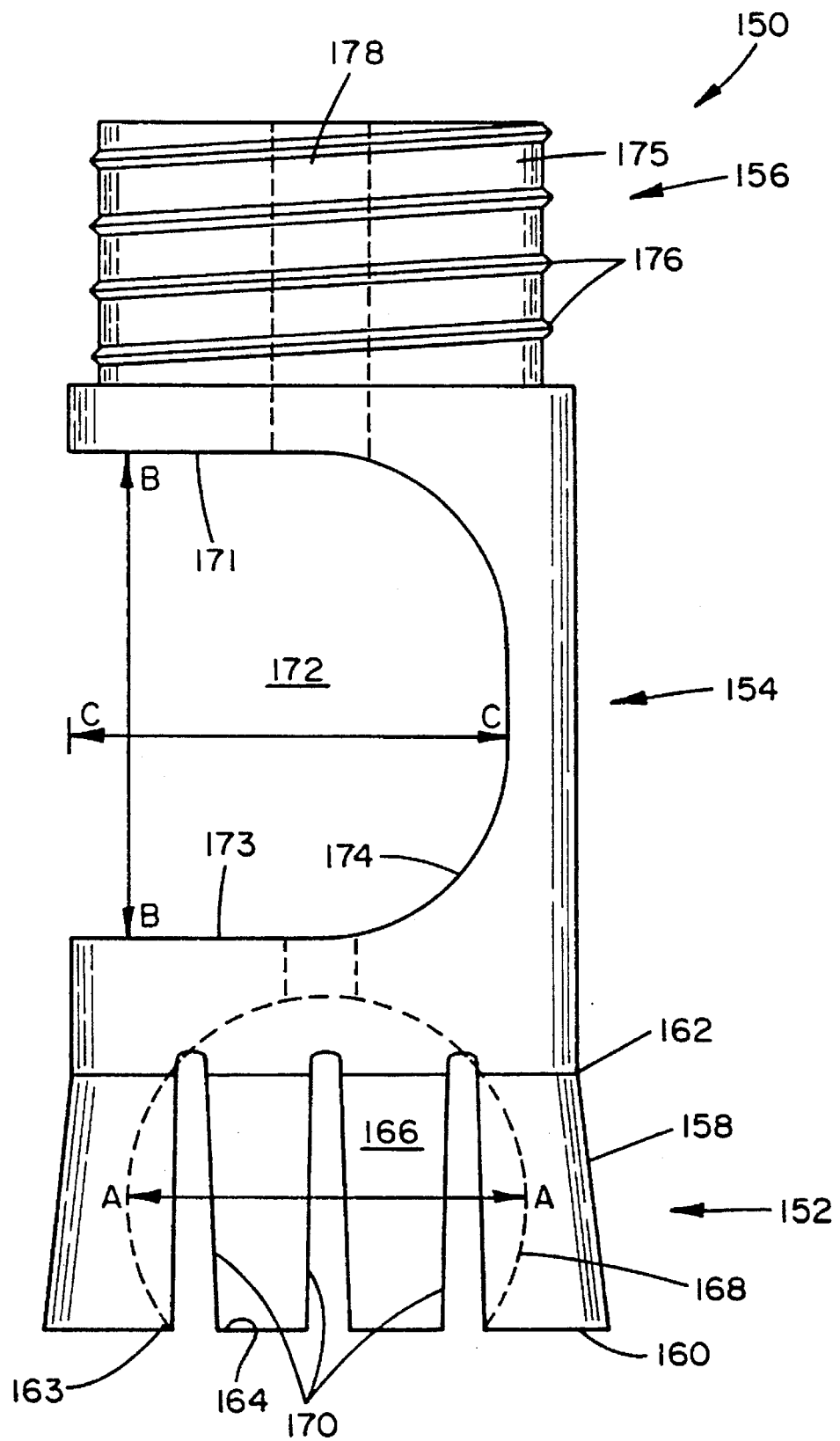
FIG. 2 is a side view of the coupling element of a first embodiment of the present invention.
Figure 3:
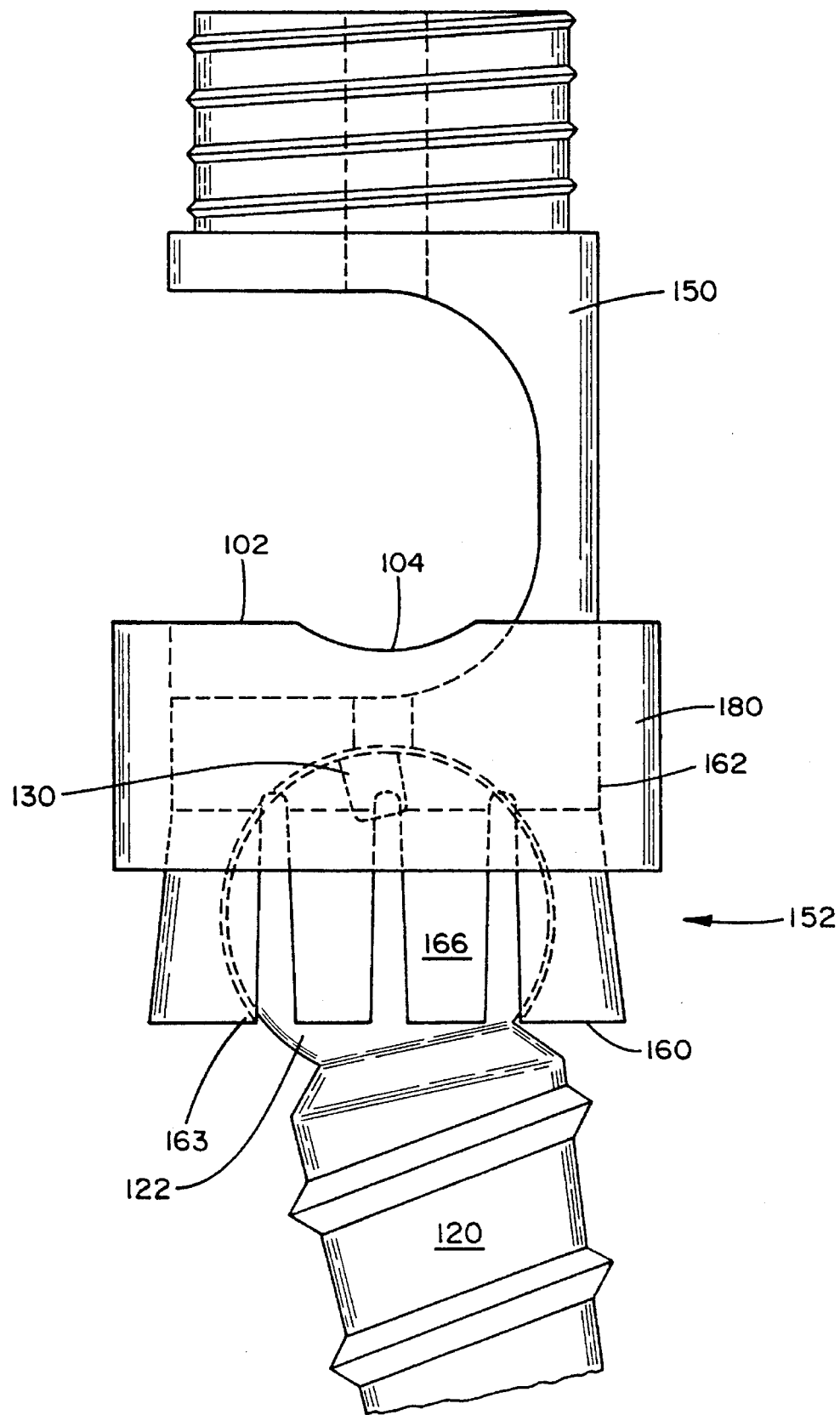
FIG. 3 is a side view of the locking collar of the present invention, shown along a direction wherein the rod seating grooves thereof are aligned perpendicular to the plane of view.

Referring now to FIG. 2, a preferred embodiment of the coupling element 150 of the present invention is shown in a side view, wherein critical features of the interior of the element are shown in phantom. The coupling element 150 comprises a generally cylindrical body which may be conceptually separated into a lower portion 152, an intermediate portion 154, and an upper portion 156, each of which shall be described more fully hereinbelow.

First, with respect to the lower portion 152, the exterior surface 158 of the body is tapered in the elongate direction such that the body is wider at the bottom 160 of the lower portion 152 than at the top 162 thereof. The bottom 160 of the element includes an opening 164, defined by annular lip 163, which forms the mouth of an interior chamber 166. The diameter of the opening 164, when otherwise unaffected by external deflecting forces, is more narrow than the maximum diameter A—A of the interior chamber 166. The interior chamber 166 has a generally curvate inner surface 168 which is correspondingly shaped to receive the semi-spherical head 122 of the screw 120.

The exterior surface of the lower portion includes a series of slots 170 which extend vertically upward from the bottom 160 of the element to a point which is closer to the top 162 of the lower portion 152 than the maximum horizontal diameter A—A. The slots 170 are provided in order that the application of an external deflecting force may widen or narrow the opening 164 therein permitting the insertion of an object which is larger than the undeflected diameter of the opening 164, or conversely, providing for the retention of an object which is smaller than the undeflected diameter of the opening 164.

The intermediate portion 154 of the generally cylindrical body of the coupling element 150 includes a large removed section which forms a horizontal channel, therein forming a rod receiving locus 172 in the side of the coupling element 150. The channel, or rod receiving locus, 172 comprises a curvate inner wall 174. In the embodiment shown in FIG. 2, the vertical distance from the top 171 of the channel 172 to the bottom 173 thereof, is larger than the diameter of the rod which is to be provided therein. This distance B—B is necessarily larger than the diameter of the rod (see FIG. 7) so that the rod may be translated upward and downward within this channel. In addition, the distance C—C which corresponds to the maximum depth of the channel 172 is set such that the support rod which is positioned in the rod receiving locus 172 nests fully within the coupling element 150, and does not extend beyond the lateral extent of the element, which would prevent a rod securing sleeve (such as shall be described with reference to FIGS. 5 and 7) from sliding into retaining relationship with the rod within the rod receiving locus 172.

The upper portion 156 of the coupling element 150 comprises a slightly narrower cylindrical core 175, having a threading 176 thereon. The upper portion 156, and the threading 176 thereon, is ideally suited for receiving a top locking nut (see FIG. 3).

A central bore 178 extends through the upper portion 156, through the intermediate portion 154, and into the lower portion 152. (As shown in the embodiment of FIG. 2, the bore 178 may be interrupted across the open spalce of the rod receiving locus 172, however, the passage defined thereby is not interrupted.) The bore 178, therefore, provides a linear passage through which a user may insert a screw-driving tool to access the interior chamber 166, and any structural elements therein.

Referring now to FIG. 3, the coupling element 150, as described more fully above with respect to FIG. 1, is shown in a side view, wherein the head 122 of the screw 120 has been received within the interior chamber 166, and a locking collar 180 is shown in its pre-locked position about the top 162 of the lower portion 152. The head 122 of the screw 120 is rotationally free to move relative to the coupling element, however, it is prevented from fully separating from the coupling element and the interior chamber 166 by the annular lip 163 at the bottom 160 of the lower portion 152. The locking collar 180 comprises a contiguous annular element having an inner diameter which is equal to or slightly larger than the outer diameter of the lower portion 152 at the top 162 thereof. In order to lock the screw 120 into an angle relative to the coupling element 150, therein eliminating the freedom of the screw 120 to swing and rotate relative to the coupling element 150, the locking collar must be forced downward relative to the coupling element 150. A dowel, protuberance, or other suitable means may be provided on the surface of the element 150 so that the collar 180 may not be easily moved upward, thereby preventing separation of the collar during handling and/or shipping, prior to use.

The top surface 102 of the locking collar includes a pair of opposing currate grooves 104 on which to receive the rod. It is the downward translation of the rod, as is set forth hereinbelow with reference to FIG. 7, which causes the locking collar 180 to descend and secure the screw 120 to the coupling element 150.

Figure 4:
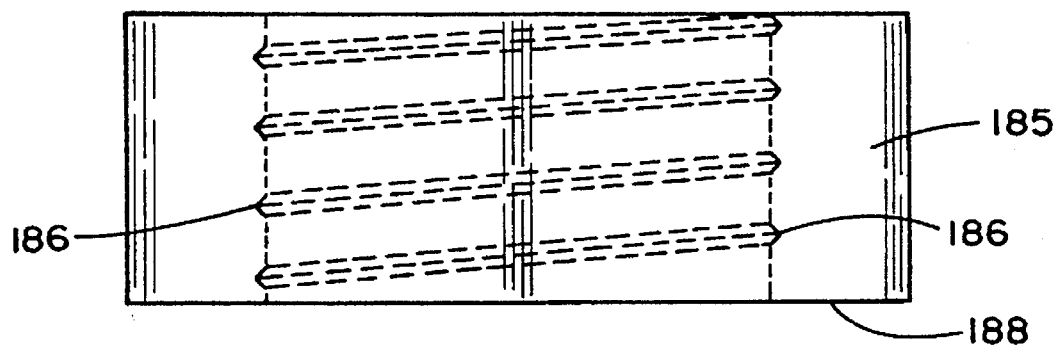
FIG. 4 is a side view of the coupling element shown in FIG. 2, having the screw shown in FIG. 1 inserted into the interior chamber therein, and including the locking collar shown in FIG. 3 in its unsecured position.
Figure 5:
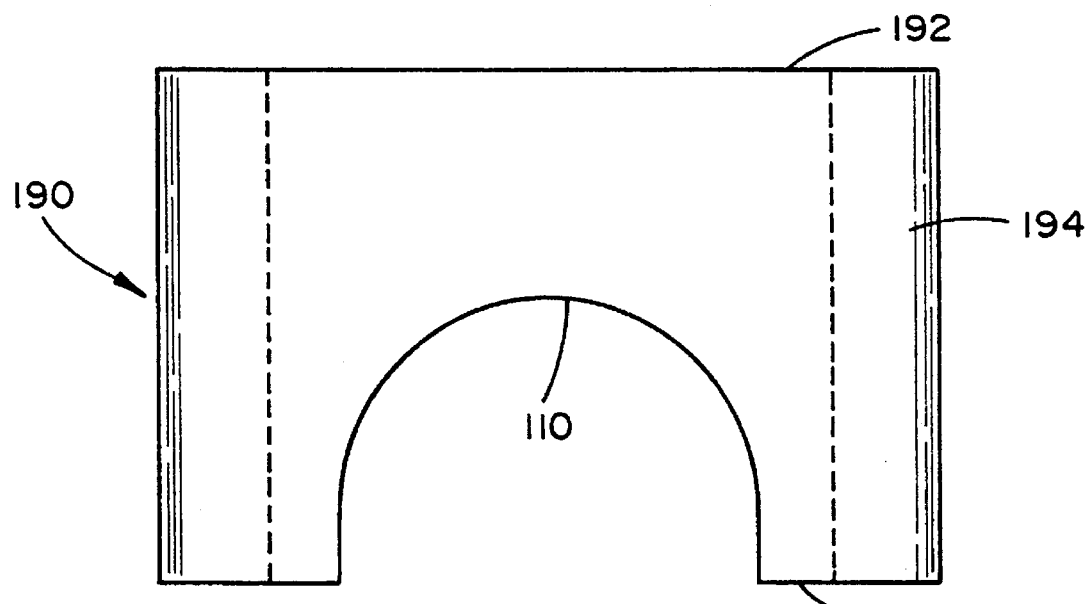
FIG. 5 is a side cross-sectional view of the top locking nut of the present invention.
Figure 6:
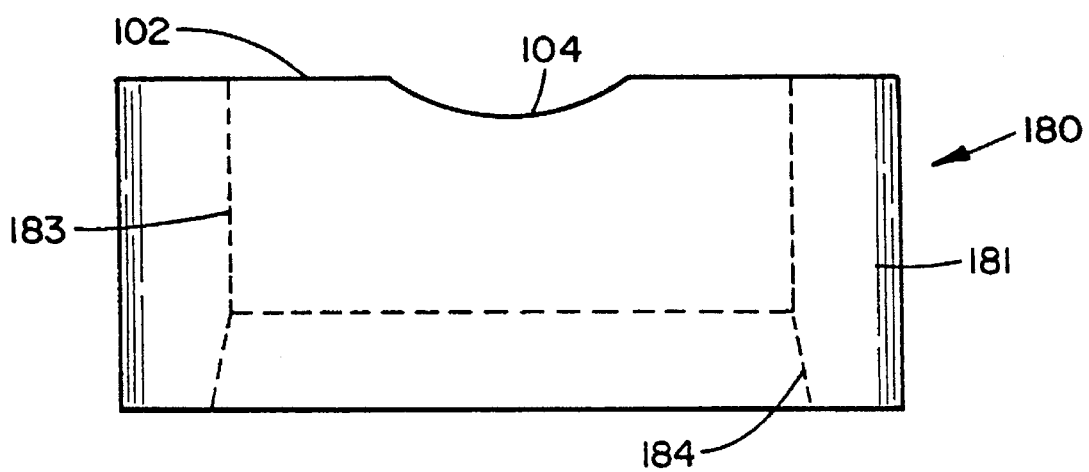
FIG. 6 is a side view of the rod securing sleeve of the first embodiment, shown along a direction wherein the rod seating grooves thereof are aligned perpendicular to the plane of view.

Referring now to FIGS. 4, 5, and 6, a top locking nut 185, the rod securing sleeve 190, and the locking collar 180 of the first embodiment are shown in respective side cross-section views.

Referring specifically to FIG. 4, the nut 185 comprises an inner threading 186 which is intended to mate with the threading 176 on the upper portion 156 of the coupling element 150. The bottom surface 188 of the nut 185 is intended to seat against the top surface 192 of the rod securing sleeve 190, but is permitted to rotate relative to the sleeve, therein providing a means for driving the sleeve downward (as more fully described hereinbelow with respect to the full assembly of the device, and with respect to FIG. 7).

Referring now specifically to FIG. 5, and the rod securing sleeve 190 shown therein, the sleeve comprises a hollow cylindrical body 194 having an interior diameter which is equal to the outer diameter of the coupling element, so that it may be placed over the coupling element. The bottom surface 111 of the rod securing sleeve 190 includes diametrically opposing grooves 110 which are positioned and designed to securely mate to the curvature of the rod which is to be positioned within the rod receiving locus 172.

Referring now to FIG. 6, the locking collar 180, as described above with respect to FIG. 3 and the initial disposition of the coupling element prior to implantation, comprises a hollow cylindrical body 181 having a pair of opposing grooves 104. The grooves 104 of the locking collar 180 are shown as having being a much shallower curve than the grooves 110 of the rod securing sleeve 190. While the radius of curvature of each pair of the grooves 104,110 is the same, it is preferable that the rod securing sleeve grooves 110 be deeper inasmuch as they are designed to lock the rod in place. While the grooves 104 of the locking collar 180 are also intended to secure the rod in place, the locking collar 180 is further designed to translate downward to lock the screw 120 to the coupling element 150. in order that the bottom lip of the rod receiving locus does not interfere with this downward. translation, the grooves 104 must be shallower.

It is further understood that it is preferable for the interior surface 183 of the locking collar 180 to include a lower outwardly tapered portion 184 so that the downward translation of the collar 180 relative to the lower portion 152 of the coupling element 150 is not hindered by any binding mechanisms associated with the moving of a sharp angled edge through a distance to engage a friction lock.

With reference now to FIG. 7, which shows a side view of the fully locked coupling element, rod, and screw system, the preferred method of implantation and assembly is described hereinbelow. First, a pre-driiied hole is provided in the bone, into which it is desired that the screw 120 be disposed. The hole may be pre-tapped, or the external threading 128 of the screw 120 may include a self-tapping lead edge. In either event, the head 122 of the screw 120 is inserted into the interior chamber 166 of the coupling element 150. At this point in the assembly process, the locking collar 180 has not yet been forced downward along the outwardly tapered lower portion 152 (as shown in FIG. 3) thereby providing the screw 120 and the coupling element 150 with the capacity to rotate relative to one another.

By orienting the coupling element 150 and the screw 120 coaxially, the central bore 178 may be aligned with the recess 130 in the head 122 of the screw 120 so that a screw-driving tool may be used to drive the screw into the preformed hole in the bone.

Subsequent to the screw 120 being driven into the hole, the coupling element 150 may be rotated relative to the screw 120, to an angle such that support rod 250 may be properly nested within the rod receiving locus 172, and disposed on the grooves 104 of the locking collar 180. After the rod 250 is appropriately positioned, the rod securing sleeve 190 is dropped over the element, such that the grooves 110 of the sleeve 190 are seated against the top of the rod 250. At this stage of the assembly, the head 122 and the coupling element 150 remain rotationally free, because the locking collar 180 remains positioned at the top 162 of the lower portion 152 of the element.

Once the proper angulation of the coupling element to the screw 120, and the secure nesting of the rod 250 between the pairs of grooves 104,110 have been established, the top locking nut 185 is threaded onto the upper portion 156 of the coupling element 150. The lower surface 188 of the nut 185 seats against the top surface 192 of the rod securing sleeve 190. As the nut 185 rotates, and descends relative to the coupling element 150, the rod securing sleeve 190 is driven downward. This motion causes the rod 250 to translate downward therein forcing the locking collar 180 to descend as well. By descending along the tapered lower portion 152 of the element, the locking collar 180 provides an inwardly directed deflecting force which causes the slots 170 in the lower portion 152 of the element to narrow so that the collar may proceed downward. This deflection inward causes the inner surface 168 of the interior chamber 166 to crush lock against the head 122 of the screw 120. This clamping force locks the angulation of the screw 120 to the coupling element 150.

In addition, the downward force of the nut 185 against the rod securing sleeve 190 and the upward resistance of the locking collar 180, once fully descended into position, causes the rod 250 to be locked between the grooves 104,110 of each. This locking prevents the rod 250 from sliding relative to the assembled structure (along an axis which is perpendicular to the plane of FIG. 7). The full insertion of the top locking nut 185, therefore, locks the rod 250 to the coupling element 150, as well as the screw 120 to the coupling element 150.

While there has been described and illustrated embodiments of a polyaxial screw and coupling element assembly for use with posterior spinal rod implantation apparatus, it will be apparent to those skilled in the art that variations and modifications are possible without deviating from the broad spirit and principle of the present invention. The present invention shall, therefore, be limited solely by the scope of the claims appended hereto.

We claim:

1. A polyaxial screw and coupling element assembly for use with orthopedic rod implantation apparatus, comprising:
   a polyaxial screw having a curvate head;
   a coupling element including; an interior chamber wherein said curvate head may be polyaxially mounted, a channel formed in a side of said coupling elemem, and a threading disposed on an upper exterior portion thereof;
   a top locking nut, mateable with said threading;
   a rod securing sleeve mountable around said coupling element; and
   a selectively translatable locking collar mounted around said coupling element.

2. The assembly as set forth in claim 1, wherein said interior chamber includes a selectively expandable and contractable opening for receiving therethrough the curvate head of said polyaxial screw.

3. The assembly as set forth in claim 2, wherein said interior chamber includes at least one vertically oriented slot, the expansion and contraction of which provides the expandable and contractable characteristic of said opening.

4. The assembly as set forth in claim 1, wherein said channel comprises a rod receiving locus.

5. A polyaxial screw and coupling element assembly for use with orthopedic rod implantation apparatus, comprising:
   a polyaxial screw having a curvate head;
   a coupling element including
      an expandable and contractable interior chamber for receiving therein said curvate head, said interior chamber further having an expandable and contractable opening for receiving therethrough said curvate head,
      a rod receiving locus, disposed in a side of said coupling element, for receiving therein a rod of said orthopedic rod implantation apparatus, and
      a surface threading disposed on an upper exterior portion thereof;
   a top locking nut, mateable with said surface threading of said upper portion;
   a rod securing sleeve, translatably mountable around said coupling element, at a position above said rod receiving locus; and
   a locking collar mounted about said coupling element,
   wherein downward translation of said top locking nut causes said rod securing sleeve to translate downward, therein causing said rod to translate downward, therein causing said locking collar to translate downward, whereby said rod is securely held within said rod receiving locus between said securing sleeve and said locking collar, and whereby said locking collar causes said expandable and contractable opening and said expandable and contractable interior chamber to crush lock against the head of said polyaxial screw.

6. The polyaxial coupling assembly as set forth in claim 5, wherein said rod securing sleeve further comprises at least one groove on a bottom surface thereof for mating with a top of said rod and wherein said locking collar further comprises at least one groove on a top surface thereof for receiving thereon said rod, whereby said downward translation of said top locking nut causes said rod to be securely held within said rod receiving locus between said grooves of said securing sleeve and said locking collar.

7. The coupling assembly as set forth in claim 5, wherein said curvate head is semi-spherical.

8. The coupling assembly as set forth in claim 5, wherein said coupling element further comprises at least one vertical slot extending upward from said opening, therein rendering said interior chamber and said opening expandable and contractable.

9. The coupling assembly as set forth in claim 3, wherein a portion of said coupling element which contains said interior chamber comprises an exterior surface taper, said portion being wider at said opening, whereby the downward translation of said locking ring causes the interior chamber and said opening to contract.

10. A orthopedic rod implantation apparatus having polyaxial screw and coupling elements, comprising:
    at least one elongate rod;
    at least one polyaxial screw having a curvate head;
    at least one coupling element including; an interior chamber wherein said curvate head may be polyaxially mounted, a channel formed in a side of said coupling element, and a threading disposed on an upper exterior portion thereof;
    at least one top locking nut, mateable with said threading;
    at least one rod securing sleeve mountable around said coupling element; and
    at least one selectively translatable locking collar mounted around said coupling element.

11. The assembly as set forth in claim 10, wherein said interior chamber includes a selectively expandable and contractable opening for receiving therethrough the curvate head of said polyaxial screw.

12. The assembly as set forth in claim 11, wherein said interior chamber includes at least one vertically oriented slot the expansion and contraction of which provides the expandable and contractable characteristic of said opening.

13. The assembly as set forth in claim 10, wherein said channel comprises a rod receiving locus.

* * * * *